(12) United States Patent
Smela et al.

(10) Patent No.: US 8,152,992 B2
(45) Date of Patent: Apr. 10, 2012

(54) CELL-BASED SENSING: BIOLOGICAL TRANSDUCTION OF CHEMICAL STIMULI TO ELECTRICAL SIGNALS (NOSE-ON-A-CHIP)

(75) Inventors: Elisabeth Smela, Silver Spring, MD (US); Pamela Ann Abshire, Silver Spring, MD (US)

(73) Assignee: University of Maryland, College Park, MD (US)

( * ) Notice: Subject to any disclaimer, the term of this patent is extended or adjusted under 35 U.S.C. 154(b) by 951 days.

(21) Appl. No.: 11/216,604

(22) Filed: Aug. 31, 2005

(65) Prior Publication Data

US 2006/0172279 A1 Aug. 3, 2006

Related U.S. Application Data

(60) Provisional application No. 60/605,936, filed on Aug. 31, 2004.

(51) Int. Cl.
*G01N 27/26* (2006.01)
*C12Q 1/02* (2006.01)

(52) U.S. Cl. ............... 205/777.5; 204/403.01; 205/792; 435/29

(58) Field of Classification Search .............. 204/403.01, 204/418, 424, 777.5, 787, 792; 435/4, 7.21, 435/287.1, 29–40.5; 436/149, 806; 257/414; 205/777.5, 787, 792
See application file for complete search history.

(56) References Cited

U.S. PATENT DOCUMENTS

| | | | |
|---|---|---|---|
| 5,675,070 A | 10/1997 | Gelperin | |
| 5,697,326 A | 12/1997 | Mottram et al. | |
| 5,788,833 A | 8/1998 | Lewis et al. | |
| 5,807,701 A | 9/1998 | Payne et al. | |
| 6,103,399 A * | 8/2000 | Smela et al. | 428/623 |
| 6,280,586 B1 * | 8/2001 | Wolf et al. | 257/253 |
| 6,322,963 B1 * | 11/2001 | Bauer | 435/4 |
| 2002/0151776 A1 * | 10/2002 | Shawgo et al. | 600/345 |
| 2003/0136960 A1 * | 7/2003 | Goodman et al. | 257/40 |
| 2003/0175744 A1 | 9/2003 | Reed et al. | |
| 2003/0207337 A1 * | 11/2003 | Han et al. | 435/7.2 |

OTHER PUBLICATIONS

Bradley, Jonathan et al., "Facilitaion of Calmodulin-Mediated Odor Adaptation by cAMP-Gated Channel Subunits." Science, 294, pp. 2176-2178. Dec. 7, 2001.*
Abshire, P., J. Lauenstein, Y. Liu, and E. Smela. 2003. Cell clinics for bioelectronic interface with single cells. *Proc. IEEE ISCAS03*. 3:618-621.
Barbee, K., S. Kwound, R. Lee, and J. Sorial. 2002. The study off a cell-based TSM piezoelectric sensor. *Proceedings of the Annual IEEE International Frequency Control Symposium*, 2002:260-267.
Barber, R.D., D.E. Jaworsky, K.W. Yau, and G.V. Ronnett. 2000. Isolation and in vitro differentiation of conditionally immortalized murine olfactory receptor neurons. *J Neurosci*. 20:3695-704.
Bozza, T.C., and J.S. Kauer. 1998. Odorant response properties of convergent olfactory receptor neurons. *J Neurosci*. 18:4560-9.

(Continued)

*Primary Examiner* — Kaj K Olsen
*Assistant Examiner* — Susan Thai
(74) *Attorney, Agent, or Firm* — Nigamnarayan Acharya; Barnes & Thornburg LLP (57) ABSTRACT

Methods and compositions for the reliable detection of chemical stimuli using a "nose-on-a-chip" are presented. The invention uses cells sensitive to chemical stimuli and detects and processes the signals given by the cells upon contact with chemical stimuli.

16 Claims, 2 Drawing Sheets

OTHER PUBLICATIONS

Calof, A.L., A. Bonnin, C. Crocker, S. Kawauchi, R.C. Murray, J. Shou, and H.H. Wu. 2002. Progenitor cells of the olfactory receptor neuron lineage. *Microsc Res Tech*. 58:176-88.

Chuah, M.I., and A.K. West. 2002. Cellular and molecular biology of ensheathing cells. *Microsc Res Tech*. 58:216-27.

Crasto, C., L. Marenco, P. Miller, and G. Shepherd. 2002. Olfactory Receptor Database: a metadata-driven automated population from sources of gene and protein sequences. *Nucleic Acids Res*. 30:354-60.

Cunningham, A.M., P.B. Manis, R.R. Reed, and G.V. Ronnett. 1999. Olfactory receptor neurons exist as distinct subclasses of immature and mature cells in primary culture. *Neuroscience*. 93:1301-12.

Eggers, M., M. Hogan, R.K. Reich, J. Lamture, D. Ehrlich, M. Hollis, B. Kosicki, T. Powdrill, K Beattie, S. Smith, and et al. 1994. A microchip for quantitative detection of molecules utilizing luminescent and radioisotope reporter groups. *Biotechniques*. 17:516-25.

Fossum, E. 1997. CMOS image sensors: Electronic camera-on-a-chip. *IEEE Transactions on Electron Devices*. 44:1689-1698.

Harrison, R., and C. Charles. 2003. A low-power low-noise CMOS amplifier for neural recording applications. *IEEE J. Solid-State Circ*. 38:958-965.

Horiuchi, T., T. Swindell, D. Sander, and P. Abshire. 2004. A low-power CMOS neural amplifier with amplitude measurements for spike sorting. *Proceedings, IEEE International Symposium on Circuits and Systems (ISCAS04)*. 4:29-32.

Jager, E.W., E. Smela, and O. Inganas. 2000. Microfabricating conjugated polymer actuators. *Science*. 290:1540-5.

Ji, H., and P. Abshire. 2005b. CMOS contact imager for monitoring cultured cells. *Proc. IEEE Int'l Symp. Cir. Sys. 2005 (ISCAS05)*.

Kafitz, K.W., and C.A. Greer. 1999. Olfactory ensheathing cells promote neurite extension from embryonic olfactory receptor cells in vitro. *Glia*. 25:99-110.

Kauer, J.S. 2002. On the scents of smell in the salamander. *Nature*. 417:336-42.

Largent, B.L., R.G. Sosnowski, and R.R. Reed. 1993. Directed expression of an oncogene to the olfactory neuronal lineage in transgenic mice. *J. Neurosci*. 13:300-12.

Lin, Y., M. Li, C.-Y. Wu, W. Hsiao, and Y. Chung. 2003. Microchips for cell-type identification. *The Seventh International Symposium on Micro Total Analysis System, 2003 (mTAS 2003)*:933-937.

Lundstrom, I. 2000. Artificial noses. Picture the smell. *Nature*. 406:682-3.

Manaresi, N., A. Romani, G. Medoro, L. Altomare, A. Leonardi, M. Tartagni, and R. Guerrieri. 2003. A CMOS chip for individual cell manipulation and detection. *IEEE J. Solid State Circ*. 38:2297-2305.

McEntire, J.K., and S.K. Pixley. 2000. Olfactory receptor neurons in partially purified epithelial cell cultures: comparison of techniques for partial purification and identification of insulin as an important survival factor. *Chem. Senses*. 25:93-101.

Persaud, K., and G. Dodd. 1982. Analysis of discrimination mechanisms in the mammalian olfactory system using a model nose. *Nature*. 299:352-5.

Reeves, N., Y. Liu, N. Neson, S. Malhotra, L.J.-M. Loganathan, J. Chaiyupatumpa, E. Smela, and P. Abshire. 2004. Integrated MEMS structures and CMOS circuits for bioelectronic interface with single cells. *IEEE ISCAS 2004: Int'l Symp. Cir. Sys*.

Roisen, F.J., K.M. Klueber, C.L. Lu, L.M. Hatcher, A. Dozier, C.B. Shields, and S. Maguire. 2001. Adult human olfactory stem cells. *Brain Res*. 890:11-22.

Romani, A., N. Manaresi, L Marzocchi, G. Medoro, A. Leonardi, L. Altomare, M. Tartagni, and R. Guerrieri. 2003. Capacitive sensor array for localization of bioparticles in CMOS lab-on-a-chip. *IEEE International Solid-State Circuits Conference*. 47:224-225, 217.

Smela, E. 1999. Microfabrication of PPy microactuators and other conjugated polymer devices. *J. Micromechanics and microengineering*, 9:1-18.

Vannelli, G.B., F. Ensoli, R. Zonefrati, Y. Kubota, A. Arcangeli, A. Becchetti, G. Camici, T. Barni, C.J. Thiele, and G.C. Balboni. 1995. Neuroblast long-term cell cultures from human fetal olfactory epithelium respond to odors. *J Neurosci*. 15:4382-94.

Willis, C.M., S.M. Church, C.M. Guest, W.A. Cook, N. McCarthy, A.J. Bransbury, M.R. Church, and J.C. Church. 2004. Olfactory detection of human bladder cancer by dogs: proof of principle study. *Bmj*. 329:712.

Young, J.M., C. Friedman, E.M. Williams, J.A. Ross, L. Tonnes-Priddy, and B.J. Trask. 2002. Different evolutionary processes shaped the mouse and human olfactory receptor gene families. *Hum Mol Genet*. 11:535-46.

Young, J.M., B.M. Shykind, R.P. Lane, L. Tonnes-Priddy, J.A. Ross, M. Walker, E.M. Williams, and B.J. Trask. 2003. Odorant receptor expressed sequence tags demonstrate olfactory expression of over 400 genes, extensive alternate splicing and unequal expression levels. *Genome Biol*. 4:R71.

Zhang, X., J. Cai, K.M. Klueber, Z. Guo, C. Lu, M. Qiu, and F.J. Roisen. 2005. Induction of oligodendrocytes from adult human olfactory epithelial-derived progenitors by transcription factors. *Stem Cells*. 23:442-53.

Zhang, X., K.M. Klueber, Z. Guo, C. Lu, and F.J. Roisen. 2004. Adult human olfactory neural progenitors cultured in defined medium. *Exp Neurol*. 186:112-23.

\* cited by examiner

CELL-BASED SENSING: BIOLOGICAL TRANSDUCTION OF CHEMICAL STIMULI TO ELECTRICAL SIGNALS (NOSE-ON-A-CHIP)

CROSS-REFERENCE TO RELATED APPLICATION

This application claims priority to 60/605,936, filed Aug. 31, 2004, entitled CELL-BASED SENSING: BIOLOGICAL TRANSDUCTION OF CHEMICAL STIMULI TO ELECTRICAL SIGNALS (NOSE-ON-A-CHIP), the entirety of which is herein incorporated by reference.

STATEMENT REGARDING FEDERALLY SPONSORED RESEARCH OR DEVELOPMENT

The subject matter of this application may in part have been funded by the National Science Foundation, ECS0225489, the United States Department of Defense, Maryland Procurement H9823004C0470, and the United States Air Force, FA95500410449. The government may have certain rights in this invention

INCORPORATION-BY-REFERENCE OF MATERIAL SUBMITTED ON A COMPACT DISC

Not Applicable.

FIELD OF THE INVENTION

The invention relates to apparatus for cell-based sensors, exploiting the exquisite capabilities of olfactory cells, to detect chemical signals.

BACKGROUND OF THE INVENTION

While a large nose is the mark of a witty, courteous, affable, generous and liberal man (at least according to Cyrano de Bergerac), an excellent sense of smell is the mark of one of nature's most exquisite senses. Olfactory sensing is exquisite because of its sensitivity, ability to detect many odorants, and ability to distinguish between odorants.

Smell has been exploited in many ways, notably to the detection of contraband and planted explosive devices. Dogs can be trained to detect unusual substances, such as explosives or narcotics. Hunting dogs search for game and search dogs search for missing people. Cadaver dogs are used to detect human remains. More recently, dogs have been successfully trained to smell out disease (Willis et al., 2004). Although dogs and their scent detecting capabilities have been extremely useful, their usefulness is limited by the need for expensive (up to tens of thousands of dollars) and time-consuming (often 2 years or more) training and limited lifetimes. Like humans, dogs can only work during limited times during the day before needing to recuperate. Human experts in various fields can also accurately detect and identify scents. For example, physicians can detect disease and conditions from the smells emitted by their patients, leading to quick and accurate diagnoses. The person on the street can easily detect a drunk by the characteristic ketones that occur as a result of alcohol metabolism, although this example is less than subtle.

The detection of odorants has also been pursued through the development of electronic noses that are used for environmental monitoring, medical testing, and food and drink production. In the most sophisticated systems, a unique chemical fingerprint can be generated by an array of sensors and then identified by pattern-recognition techniques, such as the smell of a rose (Lundstrom, 2000). Attempts to measure odors with electronic instruments were made in the 1950s, but the modern field of artificial olfaction, according to Lundstrom (Lundstrom, 2000), began in 1982 with the work of Persaud and Dodd (Persaud and Dodd, 1982). They used a small array of gas-sensitive metal-oxide devices to classify odors. While there has been a steady increase in the number of systems using chemical sensor arrays, their success depends not only on the development of new sensor technologies, but also on the availability of powerful pattern-recognition software (Lundstrom, 2000). This last aspect is particularly important for sensor arrays that produce a composite response—for detecting targets that emit a characteristic array of odorants. However, these systems suffer from many limitations that are superseded by the olfactory cells in animals.

Other examples of electronic noses, or "sniffers" include an elaborate system incorporating a testing chamber lined with arrays of gas sensors; to detect the odorants where the air pressure is lowered to create a draft into the chamber. The air that then rushes in carries the scent of the object to be identified to the sensors that detect emitted gases (Gelperin, 1997). The only gases that are detected, however, are those for which sensors are available. In another example of an electronic nose, the device consists of a chemically sensitive resistor electrically coupled to conductive elements (such as electrical leads). Arrays of these sensors in conjunction with an electrical measuring device are used to create an electronic nose for detecting analytes in fluids (Lewis and Severin, 1998). In some cases, the application of the sensor is highly specialized, such as those specifically adapted to assess the condition of cows by sensing odors emitting from their teats (Mottram and Wilkin, 1997), or to specifically detect microorganisms (Payne and Persaud, 1998).

Electronic noses have been helpful, but suffer from complex machinery and are often limited to specific applications. They require "training" to produce accurate pattern recognition. Like other calibrated instruments, electronic noses suffer from drift, causing changes in the sensor output which are not related to the presence of a stimulus and which can result in "false positive" errors. In addition, electronic sniffers suffer from fouling of the detection components, limited dynamic range, cross-sensitivity issues, and speed. Some of the complex machinery in electronic noses is required, for example, to provide reference odors, to compensate for sensor drift, or to increase the temperature using heaters in order to remove molecules from the sensor surface to refresh the surface. Circuitry or reference sensors sometimes need to be included to compensate for changes in temperature, humidity, and other environmental conditions.

SUMMARY OF THE INVENTION

In a first aspect, the invention is directed to devices for detecting a chemical stimulus. The device contains, for example, a cell that produces an electrical signal upon contact with the stimulus; at least one cell clinic on a surface of a chip for containing the cell; and an on-chip sensor for detecting the electrical signal. When the cell produces an electrical signal to the stimulus, and detecting the electrical signal correlates with the presence of the stimulus. The electrical signal can be an action potential, and the cells can be an olfactory receptor neuron or olfactory cell from an insect; the cell can also be from a cell line, and modified. The modification can consist, for example, of an exogenous odorant receptor. The chemical stimulus detected by the device can contain an osmeotope;

and the electrical signals that the cell produces when in contact with the osmeotope correlates to the concentration of the osmeotope. Furthermore, the cell can have a negative feedback mechanism that adapts to a first concentration of an osmeotope without producing an electrical signal but produces an electrical signal to a second concentration of the osmeotope. The on-chip sensor can contain, among other components, electrodes and/or and amplifier. The sensor can also contain circuitry for amplifying or detecting an action potential. Detectors can also be contained in the device for detecting action potential timing or frequencies. The chip can comprise metal oxide silicon, complementary metal oxide silicon, or other integrated semiconductor technology. The cell clinic can contain a vial position over a sensor for detecting the cell response, the vial containing, for example, more than one cell. The vial can also have an actuated lid, containing, for example, polypyrrole, and can have a semi-permeable membrane. Additional sensors can be added, including capacitance sensors, impedance sensors, resistance sensors, carbon dioxide sensors, pH sensors, ion concentration sensors, temperature sensors, fluorescence sensors, luminescence sensors, and image sensors.

In a second aspect, the invention is directed to devices for detecting a chemical stimulus distinguished by more than one osmeotope. The device can contain a first cell that produces an electrical signal upon contact with a first osmeotope, a second cell that produces an electrical signal upon contact with a second osmeotope, a first cell clinic on a surface of a chip for containing the first cell, a second cell clinic on a surface of a chip for containing the second cell, a first on-chip sensor for detecting the electrical signal of the first cell, and a second on-chip sensor for detecting the electrical signal of the second cell, wherein detecting both electrical signals correlates with the presence of the stimulus.

In a third aspect, the invention is directed to devices for detecting more than one chemical stimulus, each stimulus distinguished by a different osmeotope. The device can contain, for example, a first cell that produces an electrical signal upon contact with an osmeotope of the first stimulus, a second cell that produces an electrical signal upon contact with an osmeotope of the second stimulus, a first cell clinic on a surface of a chip for containing the first cell, a second cell clinic on a surface of a chip for containing the second cell, a first on-chip sensor for detecting the electrical signal of the first cell, and a second on-chip sensor for detecting the electrical signal of the second cell, wherein detecting the electrical signal of the first cell correlates with the presence of the first stimulus, and wherein detecting the electrical signal of the second cell correlates with the presence of the second stimulus.

In a fourth aspect, the invention is directed to methods of analyzing samples, using the devices of the invention, detecting chemical stimuli and osmeotopes.

In a fifth aspect, the invention is directed to methods of making devices for detecting a chemical stimulus or osmeotope. The method can include the steps of fabricating on a chip at least one sensor for detecting an electrical response of a cell to the chemical stimulus, fabricating at least one cell clinic on a surface of the chip for containing the cell, and loading the cell into the cell clinic.

DETAILED DESCRIPTION

The invention exploits the most selective chemical sensitivity and information processing capability known—that of biology—using cells, instead of electronic components, as sensors to transduce chemical stimuli to externally readable electrical outputs. The invention harnesses the exquisite detection capabilities of living cells, separate from an animal, such as a sniffing dog.

The invention provides compositions, devices, systems and methods for the detection of chemical stimuli, as well as their identification. Since the invention is based on the response of living cells, detection is sensitive, accurate, and precise.

Because the invention takes advantage of evolutionarily-selected receptor designs and cellular signal processing, its sensitivity, dynamic range, and precision supersede the performance of available electronic noses. The invention takes advantage of the sensory cell's amplification mechanisms, which in some cells allows for the detection of a single odorant molecule. A large dynamic range is possible because of cellular-level negative feedback, which allows the cell to adapt to a given concentration and still detect changes in concentration. The invention also exploits compartmentalization to allow for detection of complex scents—scents with components that bind different receptors and elicit signals with distinct temporal ordering and strength. The invention can employ signaling spike trains arising from different cells to determine odor identities and concentrations by correlating firing patterns with known prior information. Finally, because the invention is based on cells, miniaturization of the technology is possible.

The advantages of using the compositions, devices, systems, and methods of the invention include:
(1) highly sensitive detection of chemical stimuli;
(2) highly selective detection of chemical stimuli;
(3) detection of chemical stimuli over a broad range of concentration;
(4) increased reliability of detection;
(5) the ability to create a miniaturized system;
(6) less reliance on costly-to-train animals and possible human error; and
(7) the ability to modify the sensors for almost any olfactory application by simply changing the sensor cells, not by changing the hardware.

DEFINITIONS

Sensor cell (SC) means any cell that is capable of responding to a chemical stimulus, the response of which can be captured electronically. Olfactory neurons (ONs) are one example, as are olfactory cells (OCs) from insect antennae. Also included in the meaning of SCs are those cells that have been modified, such as by recombinant DNA technology, to express one or more receptors for chemical stimuli, or engineered such that such receptors are connected to an electronically-detectable pathway, such as a G-protein mediated pathway.

Olfactory cell means any cell from any organism relating to the sense of smell or that is capable of detecting and responding to a chemical stimulus. Olfactory cells are usually found in those parts of the organism that are responsible for detecting chemical stimuli.

Chemical stimulus means any agent that can be detected by a cell. Chemical stimuli can be organic and inorganic; multimolecular or mono-molecular. Odorants are examples of chemical stimuli.

Odorant means a substance with an odor. Odorants are detected by OCs from any organism. Thus, not all odorants are detectable by human OCs.

Osmeotope (Greek, osmeo, odor; Greek, topos, place, spot) means a portion of an odorant capable of being detected by an OC. Like epitope, which denotes a specific domain on an antigen that stimulates the production of, and is recognized by, an antibody, an osmeotope denotes a specific domain on an odorant that is recognized by an OC and is bound by a specific olfactory receptor. Each odorant can have many osmeotopes, each osmeotope being capable of being bound by a different olfactory receptor.

Contact with a chemical stimulus means that the stimulus binds to, or interacts with, a receptor on the cell.

Cell line means cells that can be cultured in vitro, dividing and reproducing for many generations (they are therefore referred to as "immortal"). Cell lines are typically clonal, usually representing a single cell genotype. Cell lines are created by introducing immortalizing genes or fragments thereof into primary cells, or are isolated from cultures of primary cells (and thus arise spontaneously), or are isolated from tumor or cancer cells.

Modified cell refers to a cell that has been altered, for example by expressing exogenous genes or gene fragments, to have desired characteristics.

Osmeotope concentration means the total number of osmeotopes per a unit volume. Thus if a sample containing a single odorant has two instances of the same osmeotope (that is, the osmeotope appears twice on the odorant molecule), then the number of osmeotopes is twice the number of odorant molecules. If an osmeotope is present only once on an odorant, than its concentration is that of the odorant. Osmeotope concentration can be also expressed as moles/liter.

Wafer, substrate mean semiconductor-based material including silicon, doped and undoped semiconductors, epitaxial layers of silicon supported by a base semiconductor or insulator foundation, three-dimensional integrated substrate comprising a layered stack of such substrates bonded together, and other semiconductor structures. Furthermore, when reference is made to a "wafer" or "substrate" in the following description, previous process steps may have been used to form regions or junctions in or over the base semiconductor structure or foundation. In addition, the semiconductor need not be silicon-based, but could be based on silicon-germanium, germanium, or gallium arsenide, among others.

Action potential means the electrical signal generated by electrically active cells, such as olfactory neurons and muscle cells. The pattern of action potentials fired by an olfactory neuron is related to the concentration of the chemical species to which it responds. Action potentials are discussed more below.

Practicing the Invention

First, exemplary devices are presented that house the biological aspects of the invention and are used to detect chemical stimuli, such as odorants. Second, biological aspects of the invention are presented. Finally, examples are provided to illustrate the invention.

The Engineering System

The engineering system has three major components: (1) closeable vials (cell clinics); (2) stimulating and sensing components; and (3) interface circuitry. After a brief example of one embodiment of a cell clinic, these three components are discussed in detail.

Figure 1:
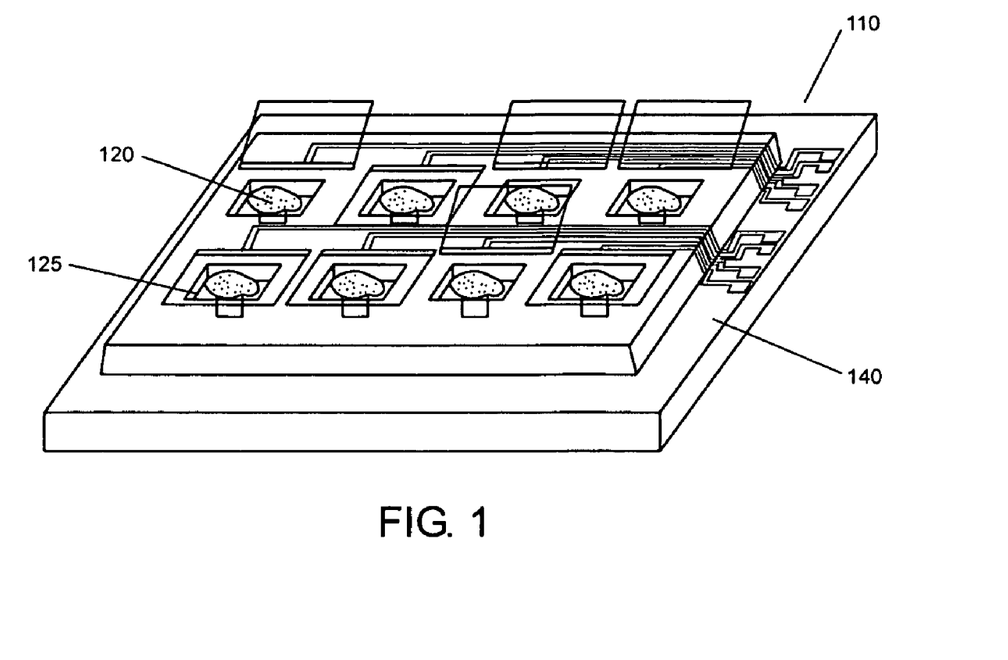
FIG. 1 shows an embodiment of a nose-on-a-chip sensor.

A chemical stimulus sensing system, or "nose-on-a-chip," contains one or more cell clinics 125 (FIG. 1) that constitute environments that contain and sustain a single cell 120 or a group of cells. Each cell clinic 125 is a meso-scale or micro-scale structure or device having a closeable cavity or vial on a substrate 140 in which at least one sensor has been defined through very large scale integration (VLSI) techniques.

Figure 2:
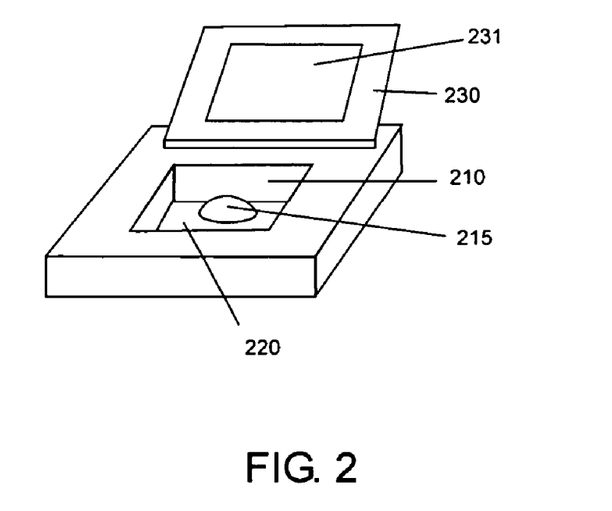
FIG. 2 shows an embodiment of a cell clinic.

FIG. 2 depicts one embodiment of a cell clinic 125. The cell clinic comprises a micro-scale vial 210 and an actuated lid 230. The cell clinic 210 provides a controlled environment that sustains the life of at least one cell 215. The cells can be monitored by feedback control of their environment within each vial 210. Environmental variables that can be monitored can include $CO_2$, temperature, and pH.

In one embodiment, an actuated lid 230 covers the vial 210 to prevent the cells from leaving the confines of the vial and thus to ensure that the cells remain properly positioned over the sensors. The actuated lid 230 can also be opened to expose cells to a sample when desired. The actuated lid 230 can include a semi-permeable membrane 231 that is used to allow molecules to pass through the lid while it is closed, such as odorants, nutrients, waste, and gases.

At the bottom of the vial are various sensors 220 to measure the electrical activity of the cell (i.e., the firing of action potentials in response to a stimulus). Other types of sensors 225 to monitor the health of the cell and/or the condition of the cell medium can also be included on the substrate. Such sensors 225 can be designed to measure cell optical activity properties, such as fluorescence, luminescence, or optical attenuation; cell electrical properties, such as capacitance, impedance, and resistance; chemical concentrations, such as ion concentration or pH; or cell metabolic activity, such as a change in temperature or pH. In the case of adherent cells, electronic monitoring can be used as a measure of cell health. Chemical sensors can be used to measure the cell environment. Optical sensors can be used to monitor cell health and environment.

The various hardware components of the nose-on-a-chip are now described. The substrates that include the sensing components and circuitry are described first, then the cell clinics, and after that the sensors and other circuitry are described in more detail.

Chips

The substrates on which cell clinics can be built include chips with integrated circuits. The most commonly used technology for integrated circuitry today is complementary metal oxide semiconductor (CMOS) technology, which is preferred because of the ability to implement a variety of circuit functions compactly.

Because of the maturity of CMOS technologies, state of the art foundry processes can be used from many manufacturers, including AMI Semiconductor (Pocatello, Id.), Agilent Technologies, Inc. (Palo Alto, Calif.), Taiwan Semiconductor Manufacturing Company Ltd. (San Jose, Calif.), and Peregrine Semiconductor Corporation (San Diego, Calif.). Specific useful technologies include AMI 1.5 micron, AMI 0.5 micron, AMI 0.35 micron, TSMC 0.35 micron, TSMC 0.25 micron, TSMC 0.18 micron, Peregrine SOS 0.5 micron, Peregrine SOS 0.25 micron, and other technologies known to those skilled in the art.

Cell Clinics, or Closeable Vials

The primary purpose of the cell clinics is to provide a place for the cells to live in a location that can be monitored by the sensor. Since the sensor is on-chip, the cell clinic needs to be physically over the chip surface. This can be achieved either by directly fabricating the cell clinics on the chip surface, or by fabricating them separately and joining them to the chip surface, either permanently or temporarily.

Preferably, the cell clinics provide a way to spatially separate cells or groups of cells (with the same or different receptors) so as not to confuse their signals, and/or to reduce cross-talk between cells above adjacent sensors and/or to ensure that the cells remain over the sensor. The cell clinics can also serve other functions, such as to provide a more natural micro-environment for cell culture, which allows the cells to function more like they naturally do in the body. The cell clinics can also contain other types of cells, such as supporting cells, which provide mechanical support, secretions, and perform other functions necessary for optimal functioning of the sensory cells.

In one embodiment of the invention, the cell clinics include vials that are positioned over the various sensors, so that the signals from the cells in that vial in response to stimuli can be clearly read by the sensor. Other sensors, such as those for chemical environment, can be positioned either inside and/or outside the vials.

The cell clinics can be semi-permeable. In other words, they can allow some things to reach the cells and not others. For example, they can allow food and waste and odor molecules to pass through, but not viruses and bacteria.

The cell clinics are preferably fabricated directly upon the surface of the substrate containing the integrated sensors and circuitry. To do this, a process must be used that is compatible with the sensors and circuitry. This can place certain constraints upon the fabrication processes, such as a maximum temperature of approximately 350° C. (to avoid damaging the underlying circuitry) and the use of surface micromachining techniques (so that as much as possible of the chip surface can be covered with sensors and circuitry).

One material that can be used to form the vials is a thick film negative photoresist such as SU-8 (available from Micro-Chem Corporation; Newton, Mass.), which can be patterned photolithographically using standard mask aligners.

Alternatively, the cell clinic can be fabricated separately and then bonded to the surface. For example, it can consist of a poly dimethyl siloxane (PDMS) well fabricated by methods known to those in the art (such as micro-molding) and joined to the surface by a method known to those in the art (such as by treatment in an oxygen plasma to render the surface of the PDMS adhesive).

Depending on the types of sensors, other processing can be done, either before or after fabrication of the vials, such as electroless plating or packaging.

In principal the vials can be any shape, such as rectangular, square, or round, but particular embodiments can require specific shapes. The dimensions of the cavities are adjusted according to cell size, number of cells in the vial, cell space and culture requirements (including gas exchange, nutrient flow, and waste discharge), and other variables, including the arrangement of the wells. For example, wells can be formed that are a few μm to several hundred μm square. The depth of the wells can range from 2 μm to 500 μm or more, more preferably the height should be appropriate for culturing SCs, such as 10-100 μm.

One way to fabricate closeable vials is through the use of lids. Lids are used to hold the cells in the chamber over the sensors, and depending on the cell type and signal, to reduce cross-talk between adjacent vials (i.e., the reading of signals in one vial from cells in an adjacent vial), among other things. The vials can be opened and closed for cell loading, exposure to sample, or other purposes. To completely mechanically and/or chemically and/or electrically seal the lids, gaskets made of a film of a conforming material, such as a rubber-like polymer, can be situated around the perimeter of the vial opening. Other methods, such as chambers separated by hydraulically actuated membranes, can also be used to control the positions of the cells and their degree of isolation.

The vials can be opened and closed by electrically controlled lids. In one embodiment, the lids can be rotated by microfabricated bilayer actuator "hinges." Such microactuators can be fabricated from conjugated polymers and noble metals. Conjugated polymers are characterized by alternating single and double bonds along the polymer backbone—a chemical structure that results in semiconductor-like properties. Conjugated polymers include polypyrrole, polyaniline, polythiophene, polyacetylene, etc. Other actuators are also possible, including other electroactive polymer actuators (such as ionic polymer-metal composites), thermal actuators, magnetic actuators, and others. Polypyrrole (PPy) actuators are preferred because they operate in almost any salt solution, including cell culture media (Jager et al., 2000). Lids can be fabricated from SU-8, BCB, polyimide, or other rigid structural materials.

To fabricate conjugated polymer microsystems, standard microfabrication procedures can be used, including surface micromachining methods that involve sequential deposition and removal (etching) steps. Such procedures are known in the art (Skotheim et al., 1998; Smela, 1999).

The actuators are designed so that they can close the vial. In the case of bilayer hinges, the thicknesses of the layers and the length and width of the actuator are designed to achieve a rotation of 180° and a final height of the bottom of the lid to be at the top of the vial, as well as to achieve sufficient force to hold in the cells and to act against any other forces that must be overcome. The actuator design that is chosen is preferably the one that takes the least chip "real estate" to meet the requirements. Therefore, a large curvature (small radius of curvature) is preferable, and this is achieved by choosing an appropriate polymer to metal thickness ratio One conjugated polymer that can be used for the actuator is PPy doped with the large immobile anion dodecylbenzene sulfonate (DBS), PPy(DBS). Methods for fabricating and actuating such actuators have been given (Smela, 1999)

Stimulating and Sensing Components

The sensors for detecting the cell signals can be implemented using custom integrated circuits and fabricated on-chip using standard technology, such as CMOS. The small electrical signals generated by the sensory cells can be detected using electrodes and appropriate circuitry.

The sensors for detecting the cell signals are fabricated on-chip, together with appropriate signal-processing circuitry. In addition, instrumentation for loading cells into the cell clinics, monitoring cell behavior and health, preparing and presenting samples to the cells, and modulating cell behavior can be integrated/fabricated on the chip. Auxiliary circuits such as potentiostats to control the MEMS actuators and radio-frequency (RF) wireless interface circuits to provide communication links and power ultra-low power circuits can also be integrated onto the same substrate as the clinics.

Detection and processing of electrical signals generated by cells in response to chemical stimuli are captured through electrodes that are close enough to the cells to detect their electrical response (action potentials). Preferably, at least one of the electrodes is within the cell clinic. These signals are then processed using CMOS circuits. Cellular electrical activity is detected using voltage amplifiers with input signals that are provided from electrodes near the site of activity. In one embodiment, the amplifier circuit is an operational transconductance amplifier in a capacitive feedback configuration, designed for a midband gain of 100. A large feedback resistance implemented by a "pseudoresistor" pFET with gate connected to drain and bulk connected to source sets the low frequency cutoff, and the ratio of feedback capacitors sets the gain. Methods for designing and integrating such amplifiers are well known in the art (Harrison and Charles, 2003; Abshire et al., 2003; Reeves et al., 2004).

While aluminum is the most commonly used metal in commercial CMOS processes, it is often not compatible for bio-interfaces. Instead, maskless, electroless plating processes are used to provide a more suitable interface metal. The metal depends in part on the cell characteristics; common metals include silver, gold, and platinum.

In addition to the amplifier, it is preferable to integrate additional signal processing circuitry to accept the electrical signals produced by the cells and produce signals corresponding to detection, classification, and quantification of the chemical agents contained in the stimuli. Specific circuits and/or processing units can be required to: (1) determine the presence of an action potential in the electrical waveform, by discriminating the amplitude, width, and/or characteristic shape of the action potential relative to noise and other interfering signals; (2) track the frequency of occurrence of action potentials in response to stimuli relative to the frequency of occurrence of action potentials in the absence of stimuli; (3) determine the timing of action potentials relative to the timing of introduction of stimuli; (4) determine the timing of action potentials relative to the timing of action potentials produced by cells in other cell clinics; (5) classify which osmeotopes are present in the stimuli on the basis of the action potential frequency and timing relationships; (6) quantify which osmeotopes are present on the basis of the action potential frequency and timing relationships; and (7) translate the identified osmeotopes and their respective concentrations into an understanding of which chemical compounds are present in the stimuli, at what concentrations. Methods for designing such algorithms and designing and fabricating such circuits and processing units are well known to those skilled in the art.

For example, the presence of an action potential can be determined using a number of algorithms and circuit implementations. If the action potential is detected on the basis of amplitude alone, the voltage of the electrical signal produced can be compared to a reference value using a circuit known as a comparator: when the voltage exceeds the reference value, an action potential is considered to have occurred. More sophisticated algorithms can offer the opportunity for improved immunity from noise and other artifacts. If the action potential is detected on the basis of amplitude and width, the amplitude and width of the waveform are compared to reference values using comparators: when the amplitude and width fall within specified ranges, an action potential is considered to have occurred. If the action potential is detected on the basis of characteristic shape, the waveform values can be compared directly to reference values, or they can be used to compute features of the waveform such as convolution with a reference template: when the features fall within specified ranges, an action potential is considered to have occurred. The other aspects of signal processing required to discriminate chemical stimuli from electrical waveforms can also be performed using algorithms implemented by integrated circuits. Methods for implementing such algorithms in integrated circuits are well known to those skilled in the art and include analog, mixed-signal, and digital processing techniques and circuits such as comparator, integrator, counter, vector multiplier, summer, bump circuit, winner-take-all, loser-take-all, filter, peak detector, trough detector, envelope detector, vector quantizer, and support vector machines, among others known to those skilled in the art. Illustrative examples can be found in (Baker and Institute of Electrical and Electronics Engineers., 2005; Cauwenberghs and Bayoumi, 1999; Cohen et al., 1998; Horiuchi et al., 2004; Liu, 2002; Sedra and Smith, 2004)

Other Sensors for Monitoring Cell Health and Environment

Cellular health and environmental conditions can be monitored using other electronic, optical, and chemical sensors included on the substrate. Electrical sensors can be used to assay cell density (by measuring resistance) and cell health (by measuring capacitance and/or impedance and/or temperature). Optical sensors can be used to assay a wide range of cellular features and properties (by measuring fluorescence or luminescence and/or by acquiring a visual image of the cells). Chemical sensors can be used to monitor the cell environment by monitoring concentrations of chemical species. Techniques for designing and fabricating such sensors are well known to those skilled in the art and specific embodiments are described in (Abshire et al., 2003; Barbee et al., 2002; Eggers et al., 1994; Fossum, 1997; Ji and Abshire, 2005a; Ji and Abshire, 2005b; Lin et al., 2003; Manaresi et al., 2003; Prakash and Abshire, 2005; Reeves et al., 2004; Romani et al., 2003).

Electrical sensors can be used to monitor a variety of quantities including resistance, capacitance, impedance, and temperature, among others known to those skilled in the art. A resistance sensor comprises at least two electrodes and an integrated circuit that measures the resistance between them, for example by applying a small current and measuring the resulting voltage, or by applying a small voltage and measuring the resulting current. An impedance sensor comprises at least two electrodes and an integrated circuit that measures the resistance and/or capacitance between them as a function of frequency. This sensor requires a means for sweeping the frequency and measuring the response. For example, the frequency can be varied using an integrated circuit known as a voltage controlled oscillator. A capacitance sensor comprises at least one electrode and an integrated circuit for determining the strength of coupling between this electrode and a nearby cell. In one embodiment, the physical principle underlying operation of the sensor is charge sharing and the electrode is formed using the topmost metal layer in an integrated circuit technology. A temperature sensor comprises an integrated circuit that measures the temperature using the physical characteristics of integrated devices such as transistors and resistors. An example of such a circuit is known as a Proportional-To-Absolute-Temperature circuit. Techniques for designing and fabricating such sensors are well known to those skilled in the art and use standard techniques of integrated circuit design.

Some electrical sensors (such as those for measuring resistance and impedance) employ electrodes that are exposed to the cell environment, whereas others (such as for measuring capacitance) employ electrodes that are not exposed to the cell environment, and others sensors (such as for measuring temperature) employ no electrodes.

Optical sensors for fluorescence or luminescence have the ability to detect emitted light of very low intensity at specific wavelengths and the ability to block light at other wavelengths which can interfere with the signal being detected. Such sensors are often used in conjunction with the application of molecules known as fluorescent probes. Many fluorescent probes have been designed to localize components within a biological specimen or to respond to a specific stimulus. Because of the maturity of fluorescent probe technology, probes can be obtained from many manufacturers, including Invitrogen (Carlsbad, Calif.), Martek Biosciences Corporation (Columbia, Md.), and Sigma-Aldrich Corporation (St. Louis, Mo.). Specific useful probes can indicate a broad set of cellular features and properties such as ion concentration, proteins, nucleic acids, pH, membrane potential, and other characteristics known to those skilled in the art.

Fluorescence sensing systems typically have at least four components: (1) a light source; (2) optical filters; (3) detectors (i.e., light sensors); and (4) signal processing circuitry. The light source is designed to deliver sufficient optical power, the filters to be capable of discriminating wavelengths, and the detectors to distinguish fluorescent emission, even in the presence of interfering excitation light. The cell must be illuminated within an appropriate range of wavelengths in order for the fluorescence to occur. This "excitation" light can be generated by a separate component integrated with the system such as a vertical-cavity surface-emitting laser (VCSEL) or a light emitting diode (LED) or by a semiconductor photon source integrated on-chip. The light can be directly shone on the cells or guided to the cells using an optical waveguide integrated on-chip.

Optical sensors for imaging the cells have the ability to measure light intensity using a dense array of photosensitive pixels. For the purposes of this invention, such sensors can be used in either a conventional imaging configuration with optical elements such as lenses that focus the image onto an imaging array as in a standard camera or light microscope, or in a "contact" imaging configuration which does not use intervening optics and which generates a representation of a specimen directly coupled to the surface of the chip. The photosensitive elements of the contact imager capture light that is transmitted through the cells. Preferably, imagers are compatible with CMOS technology to enable the implementation of other sensors and circuitry on the same substrate. Many pixel designs are suitable for imagers and are well known in the field of digital imaging technology, including passive pixels, current-mode pixels, and active pixel sensor (APS) pixels.

Chemical sensors for monitoring the cell environment typically comprise a chemically sensitive material such as a polymer, and an integrated circuit that measures the response of the chemically sensitive material. Specific embodiments typically incorporate at least one electrode on which the chemically sensitive material is patterned. The following types of CMOS-based sensors, among others, are known to those skilled in the art: pH sensors, temperature sensors, ion sensors, oxygen sensors, carbon dioxide sensors, and nitric oxide (NO) sensors.

Integrated Circuitry for Signal Conditioning, Stimulating, Interfacing and Communicating Because interface circuitry can reduce the requirements for communicating sensitive analog values over long distances, encoders can be used to reduce the required communications to the minimum necessary for the required application. For example, data converters, such as analog-to-digital, replace an analog value susceptible to additive noise, with digital values that are restored at each subsequent stage of computation or communication. Auxiliary circuits such as potentiostats to control the MEMS actuators and radio-frequency (RF) wireless interface circuits to provide communication links and provide power to ultra-low power circuits can also be integrated onto the same substrate as the clinics.

Biological Aspects

Sensor Cells (SCs)

Any SC that preferably generates an electrical signal upon interaction with a chemical stimulus can be used in the methods and compositions of the invention. To aid in the understanding of the kinds of cells—whether from primary cultures, cell lines, or modified—that can be used, a brief discussion of olfaction and signaling is given. More details can be found elsewhere, e.g., (Purves, 2004; Purves and Williams, 2001). However, this discussion is not meant to limit the invention in any manner.

1. Olfactory Epithelium and Olfactory Receptor Neurons

The transduction of olfactory information occurs in the olfactory epithelium, the sheet of neurons and supporting cells that lines approximately half of the nasal cavity. The most important members of the olfactory epithelium are the olfactory receptor neurons (ORNs), which are sensor cells that fire action potentials in response to odorants. These cells are bipolar, meaning that processes extend from the cell body in two directions. At one end is a knob-like protrusion with olfactory cilia on it. The cilia are covered with receptors that bind to particular molecular structures. Different ORNs have different receptors. In vivo the cilia extend into a mucus layer in the nasal cavity. At the other end is a small-diameter, un-myelinated axon that travels toward the brain, along the olfactory nerve to the olfactory bulb.

Because of their immediate exposure to the environment, ORNs degenerate over time and are continually replaced every 6 to 8 weeks; the cells are renewed from a population of stem cells found basally in the olfactory epithelium. Also in the olfactory epithelium are basal and sustentacular (supporting) cells.

2. Olfactory Perception in Humans

The sense of smell in humans is far less acute than in other animals, such as dogs. The difference is most likely due to numbers: other species have more ORNs, more odorant receptors (ORs), and more real estate dedicated to olfaction. Nevertheless, human smell is sensitive. For instance, the major aromatic constituent of bell pepper, 2-isobutyl-3-methoxypyrazine, can be detected at a concentration of $1\times10^{-8}$ M, although sensitivity to other odorants is lower.

Most naturally occurring odors are blends of several odorant molecules, even though they are typically experienced as a single smell. For example, the perceived scent of perfume or wine arises from a complex combination of many constituent compounds.

3. Odorant Receptors and Olfactory Coding

Olfactory receptor molecules are homologous (i.e., similar in structure or evolutionary origin) to a large family of G-protein-linked receptors that includes β-adrenergic receptors and rhodopsin. Odorant receptors have (1) seven membrane-spanning hydrophobic domains; (2) potential odorant binding sites in the extracellular domain; and (3) a carboxyl cytoplasmic domain that can interact with G-proteins. The amino acid sequences vary substantially, particularly in regions that code for the membrane-spanning domains, giving rise to a large number of different receptors. It is thought that each ORN only has a single type of receptor, although this is not firmly established.

The specificity of olfactory signal transduction results from this variety of odorant receptors present in the nasal epithelium. There are several hundred different receptors in the human nose, and up to about 1000 in other animals: in rodents, about 1,000 different odorant receptors have been identified, although in humans, the number of olfactory receptor gene sequences is only about 500-750, encoding perhaps only about 200 full-length polypeptides. While the number of receptors is small, humans can distinguish about 10,000 different odors due to the receptors acting in concert. Genetic analysis shows that each olfactory receptor neuron expresses mostly one odorant receptor. Although individual receptor neurons each express a single odorant receptor protein, the responses of mature olfactory receptor neurons are broadly tuned, responding to several different odorants with similar molecular features. In other words, the receptors recognize particular molecular structures, rather than entire odorant molecules. Therefore, a receptor responds to all molecules with that particular structure. Other parts of the molecule are recognized by different receptors. Thus, it is the pattern of response from different olfactory receptor neurons detecting different distinct molecular features that indicates which molecule has been sensed. In short, individual odorants can activate multiple receptors, and individual receptors can be activated by multiple odorants.

4. The Transduction of Olfactory Signals

As discussed above, the process of smelling begins when an odorant binds to specific receptors expressed by ORNs. Upon binding of the stimulus, the neuron depolarizes by generating an action potential. There are a number of steps that occur in the cell upon odorant binding that lead to the action potential, many of which involve amplification—this is what enables high sensitivity. In mammals, the principal pathway involves cyclic nucleotide-gated ion channels. ORNs contain an olfactory-specific G-protein ($G_{olf}$), tens of which are activated upon binding to the odorant. (This is the first stage in signal amplification.) In turn, this activates an olfactory-specific enzyme, adenylate cyclase. This enzyme catalyzes the conversion of adenosine triphosphate (ATP) into a neurotransmitter, cyclic AMP. Since the enzyme is a catalyst, a single enzyme can convert a large number of ATPs (1000/second), which is another amplification step. The resulting increase in cyclic AMP (cAMP) opens channels that permit $Na^+$ and $Ca^{2+}$ ions to enter the cell, which depolarizes the neuron. It takes three cAMPs to open a channel. The depolarization travels from the cilia to the olfactory bulb. This depolarization and its associated ion current is an electrical event, the action potential (see below) that can be detected. The amount of cAMP in the cell depends on the number of binding events, and thus on the odorant concentration. Since cAMP results in action potential (spike) generation, the number of spikes is correlated with the odorant concentration.

Like other sensory receptors, olfactory neurons "adapt" in the continued presence of a stimulus. Adaptation involves a negative feedback. In adaptation, olfactory receptor neurons have a reduced rate of action potentials in response to the continued presence of an odorant. Adaptation occurs because of: (1) increased $Ca^{2+}$ binding by the protein calmodulin, decreasing the sensitivity of the channel to cAMP; and (2) the extrusion of $Ca^{2+}$ through the activation of $Na^+/Ca^{2+}$ exchange proteins that reduce the amplitude of the receptor potential.

Receptor potential is the transmembrane potential difference of a sensory cell. Receptor potential is usually near a resting potential value, and changes around that resting potential are produced by sensory transduction or synaptic transmission from other cells. Depolarizing events cause the receptor potential to increase, generally as the result of inward current flow. The influx of current brings the membrane potential of the sensory receptor cell towards the threshold for triggering an action potential.

5. Action Potentials

The detection of the binding of a chemical stimulus to a receptor, such as an odorant to an olfactory receptor, results from action potentials—electrical excitations generated by the cell. In an action potential, the polarity of the transmembrane voltage swings rapidly from electrically negative to positive and back. Minimally, an action potential involves a spike of electrical activity: a depolarization, a re-polarization, and finally a hyper-polarization.

The transmembrane voltage changes that take place during an action potential result from changes in the permeability of the cell membrane to ions. In axons, depolarization occurs when $Na^+$ enter the axon, while re-polarization and hyper-polarization arise when $K^+$ exit. The imbalance of ions that makes possible action and resting cell potentials is maintained by cell membrane pumps, such as the sodium-potassium exchanger.

Action potentials are triggered by an initial depolarization to the point of threshold, usually around 15 mV above the resting potential. At this point, an influx of $Na^+$ opens voltage-gated $Na^+$ channels.

In un-myelinated axons, action potentials propagate as an interaction between passively spreading membrane depolarization and activation of voltage-gated sodium channels. A spatially localized depolarization opens sodium channels, allowing positive ion flux into the cell and locally depolarizing the membrane potential. This depolarization spreads to adjacent membrane via the diffusion of positive ions along the axon lumen (interior). This causes the discharge of the membrane capacitance in the adjacent membrane, and thus a depolarization of the membrane potential in that adjacent membrane. This depolarization then opens $Na^+$ channels in that location and the process repeats all the way down the axon Feedback cycles are responsible for membrane potential changes during an action potential. Membrane depolarization rapidly activates a positive feedback cycle fueled by the voltage-dependent activation of $Na^+$ conductance. This phenomenon is followed by the slower activation of a negative feedback loop as depolarization activates a $K^+$ conductance that contributes to the re-polarization of the membrane potential and termination of the action potential.

6. Cells

Any sensor cell can be used in the compositions and methods of the invention Primary cells, as well as cell lines (available from the American Type Tissue Collection (ATCC); Manassus, Va.) are useful, although cell lines are preferred because of their immortality and ease of manipulation. The preferred cell type is olfactory, preferably olfactory neurons or olfactory cells from insects, such as from *Drosophila*. The olfactory cells of insects can be located on their antennae. Cells from amphibians, such as salamander, are also useful (Kauer, 2002). Table 1 lists some examples of useful cell lines.

TABLE 1

Examples of cell lines

| Cell line name | Reference | Notes |
|---|---|---|
| None given | (Roisen et al., 2001) | Pluripotent stem cells harvested from the olfactory neuroepithelium of human cadavers; not immortalized by laboratory intervention. Produce neuronal and glial |

TABLE 1-continued

Examples of cell lines

| Cell line name | Reference | Notes |
| --- | --- | --- |
| Clones 2.2, 7.17, 5.4 | (Largent et al., 1993) | lineage cells; cAMP causes differentiation as evidenced by cells extending processes. Derived from mouse neuroepithelium immortalized with simian virus 40 T-antigen; cAMP induced morphological changes consistent with neurons in vivo. Co-culture with mouse olfactory bulb or mouse cerebral cortex had similar effects as cAMP, except bulb-co-cultured clones showed increased mitosis. |
| FNC-A6 and FNC-B4 | (Vannelli et al., 1995) | Derived from human fetal olfactory neuroepithelium; not immortalized by laboratory intervention. Cells are electrically active and responsive to odorants via a cAMP pathway. |
| 3NA12, among 38 other clones | (Barber et al., 2000) | Derived from transgenic mice which carry a transgene encoding a temperature sensitive T-antigen operably linked to a λ interferon inducible mouse major histocompatibility complex promoter. In permissive conditions, cells grow and divide; in non-permissive conditions, they differentiate. Cells are odorant-responsive |

Olfactory receptor cells can be obtained from the olfactory epithelium of vertebrate animals. The olfactory receptor neurons (ORNs) can be dissociated from the epithelium and used immediately (Bozza and Kauer, 1998). Cultures of cells obtained from organisms are known as primary cultures. In some cases, ORNs can be maintained in vitro for extended periods of time after harvest (Calof et al., 2002). ORNs can also be obtained from existing cell lines, and can be maintained in vitro for arbitrarily long periods of time. Primary cultures can be modified using techniques known in the art (see Table 1) to yield immortalized cell lines. ORNS can be modified using standard recombinant technology to express, for example, specific olfactory receptors. Modification of ORNs is desirable if olfactory receptors or components of signaling pathways are eliminated or changed during culture or immortalization.

Alternatively, cells that have been engineered to express one or more olfactory receptors can be used. For example, expression libraries of binding sites of olfactory receptors have been developed (Reed et al., 2003). These and full-length olfactory receptors can be expressed in non-neuronal cell lines. Preferably, such cell lines have signaling machinery that can integrate with the exogenous (i.e., externally originated) receptor proteins such that a detectable signal is produced. Other libraries of olfactory receptors and gene sequences are available, such as those for mouse and human (Crasto et al., 2002; Young et al., 2002; Young et al., 2003).

A method to increase confidence in the result is to load multiple cell clinics (instead of one) with the cells having the same type of receptor. If multiple vials indicate the presence of the stimulus, then the user can conclude with higher certainty that the stimulus is present.

A large variety of media formulations and conditions for generating primary cultures are well known. The selection of the media and culture conditions vary depending on cell type and can be empirically determined. To keep cells dividing, serum, such as fetal calf serum (FCS) (also known as fetal bovine serum (FBS)), is added to the medium in relatively large quantities, 5%-30% by volume, depending on cell or tissue type. Other sera include newborn calf serum (NCS), bovine calf serum (BCS), adult bovine serum (ABS), horse serum (HS), human, chicken, goat, porcine, rabbit and sheep sera. Serum replacements can also be used, such as controlled process serum replacement-type (CPSR; 1 or 3) or bovine embryonic fluid. Specific purified growth factors or cocktails of multiple growth factors can also be added or sometimes substituted for serum. Specific factors or hormones that promote proliferation or cell survival can also be used.

Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, and Medium 199. A medium specifically developed for a particular cell type/line or cell function, e.g., Madin-Darby Bovine Kidney Growth Medium, Madin-Darby Bovine Kidney Maintenance Medium, various hybridoma media, Endothelial Basal Medium, Fibroblast Basal Medium, Keratinocyte Basal Medium, and Melanocyte Basal Medium are also known. If desired, a protein-reduced or -free and/or serum-free medium and/or chemically defined, animal component-free medium can be used, e.g., CHO, Gene Therapy Medium or QBSF Serum-free Medium (Sigma Chemical Co.; St. Louis, Mo.), DMEM Nutrient Mixture F-12 Ham, MCDB (105, 110, 131, 151, 153, 201 and 302), NCTC 135, Ultra DOMA PF or HL-1 (both from Biowhittaker; Walkersville, Md.), can be used. Schneider's Drosophila Medium can also be used to support the growth of insect cell lines, among others.

Media can be supplemented with a variety of growth factors, cytokines, serum, etc., depending on the cells being cultured. Examples of suitable growth factors include: nerve growth factor (NGF), basic fibroblast growth factor (bFGF), vascular endothelial growth factor (VEGF), epidermal growth factor (EGF), transforming growth factors (TGF and TGF.B), platelet derived growth factors (PDGFs), hepatocyte growth factor (HGF), insulin-like growth factor (IGF), insulin, erythropoietin (EPO), and colony stimulating factor (CSF). Examples of suitable hormone additives are estrogen, progesterone, testosterone or glucocorticoids, such as dexamethasone. Examples of cytokine medium additives are interferons, interleukins or tumor necrosis factor-α (TNF-α). Salt solutions can also be added to the media, including Alseverr's Solution, Dulbecco's Phosphate Buffered Saline (DPBS), Earle's Balanced Salt Solution, Gey's Balanced Salt Solution (GBSS), Hanks' Balanced Salt Solution (HBSS), Puck's Saline A, and Tyrode's Salt Solution. If necessary, additives and culture components in different culture conditions be can optimized as these can alter cell response, activity, lifetime or other features affecting bioactivity.

Because of the finicky nature of neuron cells in culture, conditioned media can be used, where the media is first used to culture one cell type before being transferred to a second culture containing neuronal cells (McEntire and Pixley, 2000). For example, media can be conditioned for olfactory receptor cells by first culturing first olfactory neuronal epithelia, and then transferring the media to cultures of neuronal cells.

Specific culture conditions for specific cell lines and cultures are well known in the art, for example, such as those found in (Barber et al., 2000; Cunningham et al., 1999; Largent et al., 1993; Roisen et al., 2001; Vannelli et al., 1995; Zhang et al., 2005; Zhang et al., 2004).

If the cell clinics are not semi-permeable, the media and culture conditions can be adjusted to accommodate the restriction of nutrient and waste flow during those periods when the lids of the cell clinics are closed and the interiors are isolated from reservoirs.

Cultured cells are typically adhesive cells that require a substrate to which they are able to attach. The surface on which the cells are grown can be coated with a variety of substrates that contribute to survival, growth and/or differentiation of the cells. These substrates include laminin, EHS-matrix, collagens, poly-L-lysine, poly-D-lysine, polyomithine, and fibronectin. In some cases, extracellular matrix gels can be used, such as collagen, EHS-matrix, or gelatin (denatured collagen).

If desired, the media can be further supplemented with reagents that limit acidosis of the cultures, such as buffer addition to the medium (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glyclclycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminom-ethane (Tris), etc.). Frequent medium changes and changes in the supplied $CO_2$ (often approximately 5%) concentration can also be used to control acidosis. In some cases, because of the isolated or confined environment in the cell clinics, buffer concentrations can be adjusted to better control acidosis. For example, instead of 10 Mm or 25 Mm HEPES, 20 or 50 mM can be used.

Gases for culture typically are about 5% carbon dioxide and the remainder nitrogen, but optionally can contain varying amounts of nitric oxide (starting as low as 3 ppm), carbon monoxide and other gases, both inert and biologically active. Carbon dioxide concentrations typically range around 5%, but can vary between 2-10%. For many mammalian cells, carbon dioxide levels are usually kept in the range of 0.5% to 10%; more preferably 1% to 5%; and most preferably 2%±0.5%. However, carbon dioxide levels can be adjusted according to a cell's in vitro physiological requirements and empirically determined as necessary. Both nitric oxide and carbon monoxide, when necessary, are typically administered in very small amounts (i.e., in the parts-per-million (ppm) range), determined empirically or from the literature.

The temperature at which the cells grow optimally can be empirically determined, although the culture temperature usually is within the normal physiological range of the organism from which the cells are derived. In some cases, e.g., for storage of the cell-based sensor, cell growth and metabolism rates can be reduced by holding the cells at 0° C. to 4° C. until the sensor needs to be used, at which point they are returned to their physiologic temperature. In other cases, freeze-dried cells can be used and reconstituted before used.

In some cases, co-culturing sensing cells with other, non-sensing cells, is desired. The co-cultured cells can be used to support the growth and/or activity of the sensing cells, providing nutrients and growth factors that cannot be reproduced artificially. Examples of co-cultures include growing mammalian olfactory receptor cells with ensheathing or glial cells (Chuah and West, 2002; Kafitz and Greer, 1999) and with olfactory epithelial cells (McEntire and Pixley, 2000).

Signals

Odorant sensing by SCs can be detected and processed by monitoring the electrical activity of the cells.

EXAMPLE

The following example is for illustrative purposes only and should not be interpreted as limiting the claimed invention. There are a variety of alternative techniques and procedures available to those of skill in the art which would similarly permit one to successfully perform the intended invention.

Example 1

Integrating MEMS Structures and CMOS Circuits for Bioelectronic Interface with Single Cells (an Example of a Cell Clinic)

Microvials 100 μm×100 μm and 10 μm to 20 μm high were made of SU8 negative photoresist. The microvials were closed by SU-8/gold lids that were positioned by bilayer polymer actuators of PPy and gold. The clinics were fabricated on silicon wafers with electrodes leading to the hinges and to the interior of the vials. These structures have also been fabricated on top of custom VLSI circuitry designed to record signals from the cells within individual vials. All fabrication steps are performed at low temperature and are compatible with post-processing of the fabricated silicon die.

Because cells can escape from even deep microvials, a lid is included that can be closed after loading the cells into the vials. PPy doped with dodecylbenezenesulfonate (PPy (DBS)) is deposited over a layer of gold, which acts as the electrode through which potentials are applied as well as the constant volume layer of the bilayer, causing the bilayer to bend when the PPy changes volume. The PPy is electrochemically actuated: reducing the polymer pulls cations and water into the PPy(DBS), increasing the volume of the film, whereas oxidizing it expels the ions, decreasing the volume.

The first step in the fabrication process was to deposit and pattern a chromium layer onto an oxidized silicon wafer. Cr serves as an adhesion layer between Au and the substrate. Patterning it leaves openings for three-dimensional structures to be defined using the release method of differential adhesion. The next step was to evaporate a gold structural layer, which defines the electrodes, hinges, and lids. The structural layer was in some cases covered by a thin electroplated gold layer that roughens the surface to provide good mechanical interlocking between the PPy and gold. PPy(DBS) was electropolymerized on the hinge areas using a photoresist template; the PPy is deposited where the resist is absent. An SU-8 layer was then patterned to create lids, vials, and insulation for the wires. The gold layer was then etched in the final step to release the hinges. The hinges were attached to the substrate over those areas covered by Cr, but they were free over the areas with bare oxide since Au does not stick to silicon or silicon dioxide.

Microvials were fabricated on top of custom VLSI circuitry. An array of ten bioamplifiers was fabricated in a commercially available 0.5 µm, 3-metal, 2-poly CMOS process, with each input taken differentially between electrodes defined in the VLSI layout and a common ground. The electrodes were "probe pads," or openings in the top passivation layer that allow direct access to the metal layers. Electrodes were fabricated in two sizes, 25 µm×25 µm and 50 µm×50 µm.

The circuit was an operational transconductance amplifier in a capacitive feedback configuration, designed for a midband gain of 100 with supply voltages of +/−1.5 V. A large feedback resistance implemented by a "pseudoresistor" pFET with gate connected to drain and bulk connected to source sets the low frequency cutoff, and the ratio of feedback capacitors sets the gain.

The electrodes of the bioamplifier were fabricated using aluminum pads available in standard CMOS fabrication. The open Al electrodes of the bioamplifier were covered with electrolessly-plated gold. The electroless plating process created a rough layer with a higher surface area. Electroless plating is preferred for this purpose because electroplating requires an electrical connection to the plated surface that will reduce sensitivity and increase noise during measurement. The plating baths were obtained from Technic, Inc. (Cranston, R.I.).

The bond wires were encapsulated to prevent shorting between them when an aqueous medium is placed on the chip and to isolate the CMOS packaging materials from the living cells. A variety of encapsulation materials have been used successfully, including room temperature vulcanizing (RTV) silicone, and photopatternable polymers. For the RTV material, an opening in the center of the die was made using either a solid PDMS block, which was removed afterwards, or a hollow plastic pipette tip, which became part of the package. Silicone was also used in conjunction with a mold and cured to form an encapsulation barrier. Photopatternable polymers (Loctite® 3340; available from R.S. Hughes Company, Inc.; Sunnyvale, Calif.) were patterned using a mask and exposure to UV light to form an encapsulation barrier. A larger well was constructed using encapsulation materials and a section of plastic tube to hold the cell medium.

Biocompatibility of the materials was tested with bovine aortic smooth muscle cells (BAOSMCs). BAOSMCs stained with neutral red and cultured overnight adhered and formed cellular processes on the bottom of a fabricated vial (a silicon dioxide surface), on suitable encapsulation materials, and also on surrounding structures made of SU-8 photoresist and gold.

To test the bioamplifiers, BAOSMCs were used because they are electrically active. Primary BAOSMCs (Cell Applications, Inc.; San Diego, Calif.) were used. The test fixture was disinfected with 70% ethanol and then rinsed in sterile water. Cells were plated onto the fixture in sterile growth medium and allowed to adhere to the substrate for at least 12 hours in a humidified incubator at 37° C. in 5% $CO_2$. Testing was performed in Hank's balanced salt solution (HBSS). A ground electrode was provided by a gold wire placed in the extracellular medium. When Loctite 3340 was used for packaging, sterilization was done with ultraviolet light rather than with ethanol.

Figure 3:
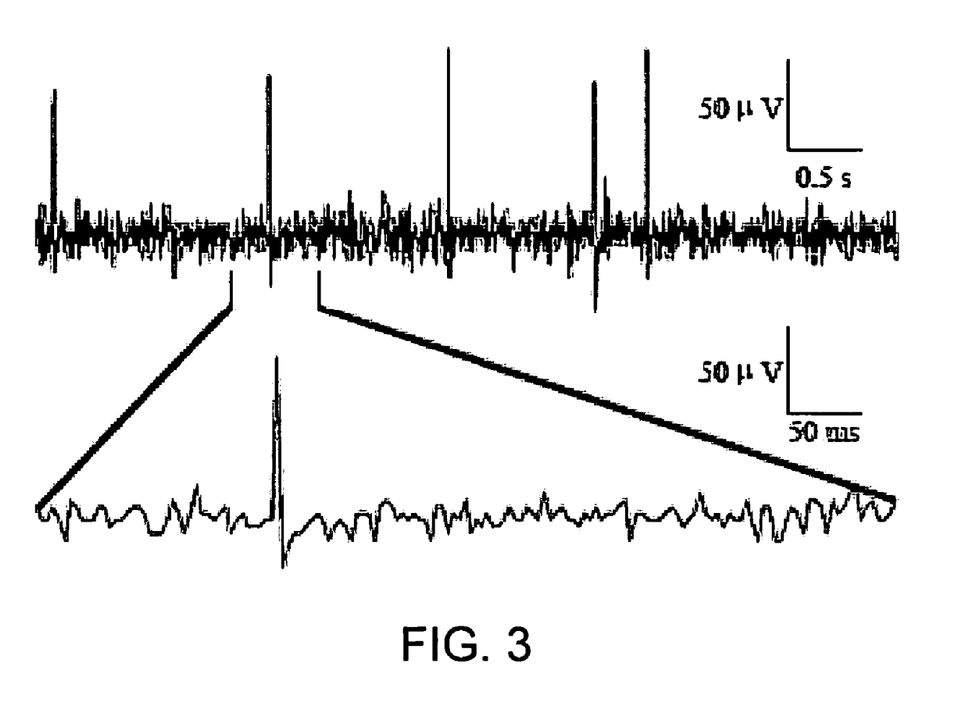
FIG. 3 shows an example of an extracellular electrical potential recorded from bovine aortic smooth muscle cells using a bioamplifier of the invention.

Extracellular signals from the cells were in the µV to mV range, and example of which is shown in FIG. 3. The bioamplifier amplified the signals from the cells and directly drove an off-chip buffer amplifier configured for unity gain. The buffered signal was monitored using an oscilloscope, and data were acquired using a GPIB interface. The size and placement of the cell relative to the recording electrode was a significant factor; the electrode should be smaller than each individual cell in order to obtain proper sealing (15-20 µm).

REFERENCES

Abshire, P., J. Lauenstein, Y. Liu, and E. Smela. 2003. Cell clinics for bioelectronic interface with single cells. *Proc. IEEE ISCAS03.* 3:618-621.

Baker, R. J., and Institute of Electrical and Electronics Engineers. 2005. CMOS circuit design, layout, and simulation. IEEE Press, New York. xxxiii, 1038 p. pp.

Barbee, K., S. Kwound, R. Lec, and J. Sorial. 2002. The study off a cell-based TSM piezoelectric sensor. *Proceedings of the Annual IEEE International Frequency Control Symposium,* 2002:260-267.

Barber, R. D., D. E. Jaworsky, K. W. Yau, and G. V. Ronnett. 2000. Isolation and in vitro differentiation of conditionally immortalized murine olfactory receptor neurons. *J Neurosci.* 20:3695-704.

Bozza, T. C., and J. S. Kauer. 1998. Odorant response properties of convergent olfactory receptor neurons. *J Neurosci.* 18:4560-9.

Calof, A. L., A. Bonnin, C. Crocker, S. Kawauchi, R. C. Murray, J. Shou, and H. H. Wu. 2002. Progenitor cells of the olfactory receptor neuron lineage. *Microsc Res Tech.* 58:176-88.

Cauwenberghs, G., and M. A. Bayoumi. 1999. Learning on silicon: adaptive VLSI neural systems. Kluwer Academic, Boston. vii, 425 p. pp.

Chuah, M. I., and A. K. West. 2002. Cellular and molecular biology of ensheathing cells. *Microsc Res Tech.* 58:216-27.

Cohen, M., P. Abshire, J. Lubkin, and G. Cauwenberghs. 1998. Analog learning fuzzy ART microchips. In Adaptive resonance theory microchips. T. Serrano-Gotarredona, B. Linares-Barranco, and A. G. Andreou, editors. Kluwer Academic Publishers, Boston. 145-166.

Crasto, C., L. Marenco, P. Miller, and G. Shepherd. 2002. Olfactory Receptor Database: a metadata-driven automated population from sources of gene and protein sequences. *Nucleic Acids Res.* 30:354-60.

Cunningham, A. M., P. B. Manis, R. R. Reed, and G. V. Ronnett. 1999. Olfactory receptor neurons exist as distinct subclasses of immature and mature cells in primary culture. *Neuroscience.* 93:1301-12.

Eggers, M., M. Hogan, R. K. Reich, J. Lamture, D. Ehrlich, M. Hollis, B. Kosicki, T. Powdrill, K. Beattie, S. Smith, and et al. 1994. A microchip for quantitative detection of molecules utilizing luminescent and radioisotope reporter groups. *Biotechniques.* 17:516-25.

Fossum, E. 1997. CMOS image sensors: Electronic camera-on-a-chip. *IEEE Transactions on Electron Devices.* 44:1689-1698.

Gelperin, A. U.S. Pat. No. 5,675,070. 1997. Olfactory sensor identification system and method.

Harrison, R., and C. Charles. 2003. A low-power low-noise CMOS amplifier for neural recording applications. *IEEE J. Solid-State Circ.* 38:958-965.

Horiuchi, T., T. Swindell, D. Sander, and P. Abshire. 2004. A low-power CMOS neural amplifier with amplitude measurements for spike sorting. *Proceedings, IEEE International Symposium on Circuits and Systems (ISCAS04)*. 4:29-32.

Jager, E. W., E. Smela, and O. Inganas. 2000. Microfabricating conjugated polymer actuators. *Science*. 290:1540-5.

Ji, H., and P. Abshire. 2005a. Chapter 1: Fundamentals of Silicon-Based Photo-transduction. In CMOS Imagers: From Photo-transduction to Image Processing. O. Yadid-Pecht and R. Etienne-cummings, editors. Kluer Academic, Norwell, Mass.

Ji, H., and P. Abshire. 2005b. CMOS contact imager for monitoring cultured cells. *Proc. IEEE Int'l Symp. Cir. Sys.* 2005 *(ISCAS05)*.

Kafitz, K. W., and C. A. Greer. 1999. Olfactory ensheathing cells promote neurite extension from embryonic olfactory receptor cells in vitro. *Glia*. 25:99-110.

Kauer, J. S. 2002. On the scents of smell in the salamander. *Nature*. 417:336-42.

Largent, B. L., R. G. Sosnowski, and R. R. Reed. 1993. Directed expression of an oncogene to the olfactory neuronal lineage in transgenic mice. *J Neurosci*. 13:300-12.

Lewis, N., and E. Severin. U.S. Pat. No. 5,788,833. 1998. Sensors for detecting analytes in fluids.

Lin, Y., M. Li, C.-Y. Wu, W. Hsiao, and Y. Chung. 2003. Microchips for cell-type identification. *The Seventh International Symposium on Micro Total Analysis System, 2003 (μTAS 2003)*:933-937.

Liu, S.-C. 2002. Analog VLSI: circuits and principles. MIT Press, Cambridge, Mass. xx, 434 p. pp.

Lundstrom, I. 2000. Artificial noses. Picture the smell. *Nature*. 406:682-3.

Manaresi, N., A. Romani, G. Medoro, L. Altomare, A. Leonardi, M. Tartagni, and R. Guerrieri. 2003. A CMOS chip for individual cell manipulation and detection. *IEEE J. Solid-State Circ.* 38:2297-2305.

McEntire, J. K., and S. K. Pixley. 2000. Olfactory receptor neurons in partially purified epithelial cell cultures: comparison of techniques for partial purification and identification of insulin as an important survival factor. *Chem Senses*. 25:93-101.

Mottram, T., and A. Wilkin. U.S. Pat. No. 5,697,326. 1997. Examination of ruminant animals.

Payne, P., and K. Persaud. U.S. Pat. No. 5,807,701. 1998. Method and apparatus for detecting microorganisms.

Persaud, K., and G. Dodd. 1982. Analysis of discrimination mechanisms in the mammalian olfactory system using a model nose. *Nature*. 299:352-5.

Prakash, S., and P. Abshire. 2005. A CMOS capacitance sensor for cell adhesion characterization. *Proc. IEEE Int'l Symp. Cir. Sys.* 2005 *(ISCAS05)*.

Purves, D. 2004. Neuroscience. Sinauer Associates, Publishers, Sunderland, Mass. 1 v. (various pagings) pp.

Purves, D., and S. M. Williams. 2001. Neuroscience. Sinauer Associates, Sunderland, Mass. xviii, 681, [16, 3, 25] p. pp.

Reed, R. R., K. W. Yau, and D. Krautwurst. U.S. Patent Application Publication 20030175744 2003. Olfactory receptor expression libraries and methods of making and using them Reeves, N., Y. Liu, N. Neson, S. Malhotra, L. J.-M. Loganathan, J. Chaiyupatumpa, E. Smela, and P. Abshire. 2004. Integrated MEMS structures and CMOS circuits for bioelectronic interface with single cells. *IEEE ISCAS* 2004: *Int'l Symp. Cir. Sys.*

Roisen, F. J., K. M. Klueber, C. L. Lu, L. M. Hatcher, A. Dozier, C. B. Shields, and S. Maguire. 2001. Adult human olfactory stem cells. *Brain Res*. 890:11-22.

Romani, A., N. Manaresi, L. Marzocchi, G. Medoro, A. Leonardi, L. Altomare, M. Tartagni, and R. Guerrieri. 2003. Capacitive sensor array for localization of bioparticles in CMOS lab-on-a-chip. *IEEE International Solid-State Circuits Conference*. 47:224-225, 217.

Sedra, A. S., and K. C. Smith. 2004. Microelectronic circuits. Oxford University Press, New York. 1 v. (various pagings) pp.

Skotheim, T. A., R. L. Elsenbaumer, and J. R. Reynolds. 1998. Handbook of conducting polymers. M. Dekker, New York. xiii, 1097 p. pp.

Smela, E. 1999. Microfabrication of PPy microactuators and other conjugated polymer devices. *J. Micromechanics and microengineering*. 9:1-18.

Vannelli, G. B., F. Ensoli, R. Zonefrati, Y. Kubota, A. Arcangeli, A. Becchetti, G. Camici, T. Barni, C. J. Thiele, and G. C. Balboni. 1995. Neuroblast long-term cell cultures from human fetal olfactory epithelium respond to odors. *J Neurosci*. 15:4382-94.

Willis, C. M., S. M. Church, C. M. Guest, W. A. Cook, N. McCarthy, A. J. Bransbury, M. R. Church, and J. C. Church. 2004. Olfactory detection of human bladder cancer by dogs: proof of principle study. *Bmj*. 329:712.

Young, J. M., C. Friedman, E. M. Williams, J. A. Ross, L. Tonnes-Priddy, and B. J. Trask. 2002. Different evolutionary processes shaped the mouse and human olfactory receptor gene families. *Hum Mol Genet*. 11:535-46.

Young, J. M., B. M. Shykind, R. P. Lane, L. Tonnes-Priddy, J. A. Ross, M. Walker, E. M. Williams, and B. J. Trask. 2003. Odorant receptor expressed sequence tags demonstrate olfactory expression of over 400 genes, extensive alternate splicing and unequal expression levels. *Genome Biol*. 4:R71.

Zhang, X., J. Cai, K. M. Klueber, Z. Guo, C. Lu, M. Qiu, and F. J. Roisen. 2005. Induction of oligodendrocytes from adult human olfactory epithelial-derived progenitors by transcription factors. *Stem Cells*. 23:442-53.

Zhang, X., K. M. Klueber, Z. Guo, C. Lu, and F. J. Roisen. 2004. Adult human olfactory neural progenitors cultured in defined medium. *Exp Neurol*. 186:112-23.

We claim:

1. A device for detecting an odorant, comprising:
   a cell that produces action potentials upon contact with the odorant; and
   an on-chip sensor for detecting the action potentials by measuring extracellular changes in voltage or current,
   wherein the cell is selected from the group consisting of olfactory neurons, olfactory cells from insect antennae, and cells that have been engineered to respond by producing the action potentials upon contact with the odorant.

2. The device of claim 1, wherein the cell is from a cell line.

3. The device of claim 1, wherein the action potentials produced by the cell correlate with the concentration of the odorant.

4. The device of claim 1, wherein the cell's DNA encodes a negative feedback mechanism that temporarily reduces the rate of production of the actions potentials in response to continued exposure to the odorant.

5. The device of claim 1, wherein the on-chip sensor for detecting the action potentials of the cell comprises electrodes.

6. The device of claim 1, wherein the on-chip sensor for detecting the action potentials of the cell comprises an amplifier.

7. The device of claim 1, wherein the on-chip sensor for detecting the action potentials of the cell comprises circuitry for discriminating the amplitude, width, or shape of the action potentials.

8. The device of claim 1, further comprising detectors for detecting timing and frequencies of the action potentials.

9. The device of claim 1, wherein the chip comprises at least one of a metal oxide semiconductor circuit, a complementary metal oxide semiconductor circuit, or other integrated semiconductor circuit.

10. The device of claim 1, wherein the at least one additional sensor is selected from the group consisting of a capacitance sensor, an impedance sensor, a resistance sensor, a carbon dioxide sensor, a pH sensor, an ion concentration sensor, a temperature sensor, a fluorescence sensor, a luminescence sensor, and an image sensor.

11. A method of analyzing a sample, comprising: introducing the sample into the device of claim 1 and assaying the cell for a response to the odorant,
wherein detecting a response correlates with the presence of the odorant.

12. The method of claim 11, further comprising correlating the response to a reference value to determine the identity of the odorant.

13. The method of claim 11, wherein the cell is selected from the group consisting of olfactory neurons, olfactory cells from insect antennae, and cells that have been engineered to respond by producing the action potentials upon contact with the odorant.

14. A device for detecting an odorant, comprising:
a first cell that produces an action potentials upon contact with a first osmeotope of the odorant,
a second cell that produces an action potentials upon contact with a second osmeotope of the odorant,
a first on-chip sensor for detecting the action potentials of the first cell; and a second on-chip sensor for detecting the action potentials of the second cell;
wherein the cells are selected from the group consisting of olfactory neurons, olfactory cells from insect antennae, and cells that have been engineered to respond by producing the action potentials upon contact with an odorant; and detecting the action potentials from the first cell and the actions potentials from the second cell correlate with the presence of the odorant.

15. A device, for detecting two odorant, each odorant distinguished by a different osmeotope, comprising:
a first cell that produces action potentials upon contact with an osmeotope of the first odorant;
a second cell that produces an action potentials upon contact with an osmeotope of the second odorant;
a first cell clinic on a surface of a chip for containing the first cell; a second cell clinic on a surface of a chip for containing the second cell;
a first on-chip sensor for detecting the action potentials of the first cell; and
a second on-chip sensor for detecting the action potentials of the second cell;
wherein the cells are selected from the group consisting of olfactory neurons, olfactory cells from insect antennae, and cells that have been engineered to respond by producing the action potentials upon contact with the odorant;
wherein detecting the action potentials of the first cell correlates with the presence of the first odorant; and
wherein detecting the action potential of the second cell correlates with the presence of the second odorant.

16. A method of making a device for detecting a chemical odorant, comprising:
fabricating on a chip at least one sensor for detecting an action potential of a cell that produces an action potential in response to the odorant; and
loading the cell to be in proximity to the sensor; wherein the cell is selected from the group consisting of olfactory neurons, olfactory cells from insect antennae, and cells that have been engineered to respond by producing the action potentials upon contact with the odorant.

* * * * *